(12) United States Patent
Paul et al.

(10) Patent No.: US 10,463,586 B2
(45) Date of Patent: Nov. 5, 2019

(54) HAIR SHAPING COMPOSITION

(71) Applicant: Conopco, Inc., Englewood Cliffs, NJ (US)

(72) Inventors: Prem Kumar Cheyalazhagan Paul, Wirral (GB); Susan Pye, Wirral (GB)

(73) Assignee: CONOPCO, INC., Englewood Cliffs, NJ (US)

( * ) Notice: Subject to any disclaimer, the term of this patent is extended or adjusted under 35 U.S.C. 154(b) by 0 days.

(21) Appl. No.: 15/526,060

(22) PCT Filed: Nov. 10, 2015

(86) PCT No.: PCT/EP2015/076214
§ 371 (c)(1),
(2) Date: May 11, 2017

(87) PCT Pub. No.: WO2016/078970
PCT Pub. Date: May 26, 2016

(65) Prior Publication Data
US 2017/0304166 A1 Oct. 26, 2017

(30) Foreign Application Priority Data
Nov. 17, 2014 (EP) .................................. 14193420

(51) Int. Cl.
*A61Q 5/04* (2006.01)
*A61K 8/34* (2006.01)
*A61K 8/33* (2006.01)
*A61K 8/42* (2006.01)
*A61K 8/39* (2006.01)

(52) U.S. Cl.
CPC ............... *A61K 8/345* (2013.01); *A61K 8/33* (2013.01); *A61K 8/39* (2013.01); *A61K 8/42* (2013.01); *A61Q 5/04* (2013.01)

(58) Field of Classification Search
None
See application file for complete search history.

(56) References Cited

U.S. PATENT DOCUMENTS

| | | | | |
|---|---|---|---|---|
| 3,650,280 A | * | 3/1972 | Roberts ................... | A61K 8/33 132/202 |
| 4,080,310 A | * | 3/1978 | Ng .......................... | A61K 8/44 424/70.17 |
| 4,338,295 A | | 7/1982 | Highley et al. | |
| 5,181,529 A | | 1/1993 | Roberts | |

(Continued)

FOREIGN PATENT DOCUMENTS

| | | | | |
|---|---|---|---|---|
| KR | 20100013791 | | 2/2010 | |
| KR | 20100013791 | * | 6/2011 | ............. A61Q 17/00 |

OTHER PUBLICATIONS

KR20100013791 East translation.*

(Continued)

*Primary Examiner* — Nicole P Babson
*Assistant Examiner* — Lori K Mattison
(74) *Attorney, Agent, or Firm* — Foley & Lardner LLP

(57) ABSTRACT

The invention provides a hair shaping composition suitable for topical application to hair, the composition comprising from 1 to 25 wt % of one or more $C_{2-4}$ monoaldehydes and from 1 to 25 wt % of one or more urea compounds; dissolved or dispersed in an aqueous carrier.

12 Claims, 1 Drawing Sheet

Control

3% UREA & 3% Glyceraldehyde

(56) References Cited

U.S. PATENT DOCUMENTS

| | | | |
|---|---|---|---|
| 5,993,787 A * | 11/1999 | Sun | A61K 8/34 424/401 |
| 2006/0024917 A1 * | 2/2006 | Henley | H01L 21/2007 438/455 |
| 2009/0126756 A1 | 5/2009 | Syed et al. | |
| 2009/0165812 A1 | 7/2009 | Resnick et al. | |
| 2013/0255009 A1 * | 10/2013 | Hu | A61K 8/362 8/425 |
| 2014/0322283 A1 | 10/2014 | Berthier et al. | |

OTHER PUBLICATIONS

KR20100013791 Google translation.*
IPRP in PCTEP2015076214, dated Feb. 28, 2017.
Search Report & Written Opinion in PCTEP2015076214, dated Jan. 27, 2016.
Search Report in EP14193420, dated May 20, 2015.
Written Opinion in EP14193420, dated May 20, 2015.

* cited by examiner

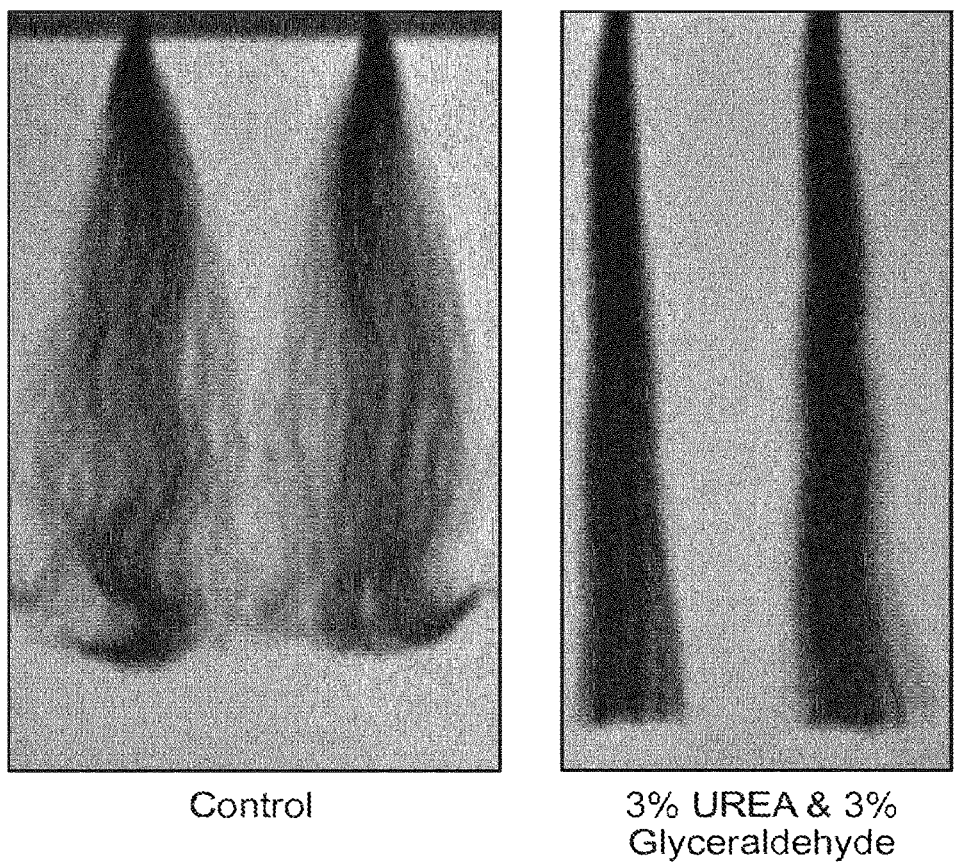

HAIR SHAPING COMPOSITION

FIELD OF THE INVENTION

This invention relates to a hair shaping composition, and more particularly a hair shaping composition which does not require the breakage of hair disulfide bonds.

BACKGROUND AND PRIOR ART

Many people with naturally kinky, curly, or even wavy hair often desire to straighten their hair. Permanent hair straightening compositions that are on the market are based on chemical treatment of the hair in a two-step process using reducing agents to break hair disulfide bonds, followed by a neutralisation or oxidation step to re-establish new disulfide bonds in the desired configuration. Such systems have various negatives associated with them; in that the process itself is difficult to conduct, in many instances this straightening process is undertaken by a qualified hairdresser in a professional salon. Furthermore the straightening process damages the hair, has an unpleasant odour and can cause irritation to the scalp.

Surprisingly we have found that hair can be shaped without causing the chemical damage which is traditionally associated with permanent hair straightening processes involving breakage of the hair disulfide bonds. Advantageously the method of the invention can be accomplished by a consumer without intervention of a professional hairdresser. Furthermore, hair shaped with the method of the invention remains shaped even after subsequent washing.

SUMMARY OF THE INVENTION

The present invention provides a hair shaping composition suitable for topical application to hair, the composition comprising from 1 to 25 wt % of one or more $C_{2-4}$ monoaldehydes and from 1 to 25 wt % of one or more urea compounds; dissolved or dispersed in an aqueous carrier.

The invention also provides a method for shaping hair which comprises the following steps:
(i) treating the hair by topical application of a hair shaping composition as defined above, and
(ii) mechanically shaping the treated hair.

DETAILED DESCRIPTION AND PREFERRED EMBODIMENTS

Suitable $C_{2-4}$ monoaldehydes for use in the invention are aliphatic monoaldehydes of the general formula:

$$X—(CHY)_n CHO$$

in which n is an integer of from 1 to 3;
X is —H or —OH, and
each Y is independently selected from —H and —OH.
Preferred $C_{2-4}$ monoaldehydes of the above general formula include at least one —OH group and more preferably two —OH groups.

A particularly preferred $C_{2-4}$ monoaldehyde for use in the invention is glyceraldehyde.

Mixtures of any of the above compounds may also be used.

Preferably the level of $C_{2-4}$ monoaldehyde in the composition of the invention ranges from 1 to 10 wt % and more preferably from 1 to 5 wt %, by total weight $C_{2-4}$ monoaldehyde based on the total weight of the composition.

Suitable urea compounds for use in the invention in the composition have the general formula:

$$\begin{matrix} R1 & & R4 \\ \diagdown & & \diagup \\ N—CO—N & \\ \diagup & & \diagdown \\ R2 & & R3 \end{matrix}$$

in which R1, R2, R3 and R4 are each independently selected from hydrogen, $C_1$-$C_4$ alkyl groups and $C_2$-$C_6$ hydroxyalkyl groups (which may contain from 1 to 5 hydroxyl groups).

The term "alkyl" in the context of this invention generally denotes a saturated, linear or branched hydrocarbon chain.

Preferably R1, R2, R3 and R4 are each independently selected from hydrogen, methyl, ethyl and hydroxyethyl.

More preferably R1, R2, R3 and R4 are each hydrogen.

Mixtures of any of the above compounds may also be used.

Preferably the level of urea compound in the composition of the invention ranges from 1 to 10 wt % and more preferably from 1 to 5 wt %, by total weight urea compound based on the total weight of the composition.

The weight ratio of $C_{2-4}$ monoaldehyde to urea compound in the composition of the invention preferably ranges from 5:1 to 1:2, more preferably from 3:1 to 2:3, and is most preferably from about 1:1.

Advantageously, the hair shaping composition of the invention does not require the incorporation of reducing agents, and a hair shaping composition according to the invention is generally substantially free of such materials. The term "substantially free" in the context of this invention means that reducing agents are absent or included in trace quantities only, such as no more than 0.1 wt %, preferably no more than 0.01 wt %, and more preferably from 0 to 0.001 wt % (by weight based on the total weight of the composition).

The term "reducing agent" in the context of this invention means an agent which is effective to break hair disulfide bonds when applied to hair for a period ranging from about 3 to 15 minutes and at a temperature ranging from about 20 to 30° C. Examples of such reducing agents are ammonium thioglycolate (in a solution having a pH of between about 7 and 10.5), glyceryl monothioglycolate (employed at a pH of less than 7), thioglycolic acid, dithioglycolic acid, mercaptoethyl amine, mercaptopropionic acid, dithioglycolate and alkali metal or ammonium sulfites or bisulfites.

A hair shaping composition according to the invention will generally comprise at least 60 wt %, preferably at least 70 wt % and more preferably at least 80 wt % water (by weight based on the total weight of composition). Preferably, the composition comprises no more than 99 wt % and more preferably no more than 98 wt % water (by weight based on the total weight of the composition). Other organic solvents may also be present, such as lower alkyl alcohols and polyhydric alcohols. Examples of lower alkyl alcohols include $C_1$ to $C_6$ monohydric alcohols such as ethanol and isopropanol. Examples of polyhydric alcohols include propylene glycol, hexylene glycol, glycerin, and propanediol. Mixtures of any of the above described organic solvents may also be used.

A hair shaping composition according to the invention may suitably have a conditioning gel phase, which may be generally characterized as a gel (Lβ) surfactant mesophase consisting of surfactant bilayers. Such a conditioning gel phase may be formed from a cationic surfactant, a high melting point fatty alcohol and an aqueous carrier. Typically these components are heated to form a mixture, which is cooled under shear to room temperature. The mixture undergoes a number of phase transitions during cooling, normally resulting in a gel ($L_\beta$) surfactant mesophase consisting of surfactant bilayers.

Examples of suitable cationic surfactants which are useful for forming the conditioning gel phase include quaternary ammonium cationic surfactants corresponding to the following general formula:

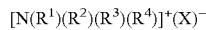

$$[N(R^1)(R^2)(R^3)(R^4)]^+(X)^-$$

in which $R^1$, $R^2$, $R^3$, and $R^4$ are each independently selected from (a) an aliphatic group of from 1 to 22 carbon atoms, or (b) an aromatic, alkoxy, polyoxyalkylene, alkylamido, hydroxyalkyl, aryl or alkylaryl group having up to 22 carbon atoms; and X is a salt-forming anion such as those selected from halide, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

Specific examples of such quaternary ammonium cationic surfactants of the above general formula are cetyltrimethylammonium chloride, behenyltrimethylammonium chloride (BTAC), cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, dipalmitoylethyldimethylammonium chloride, PEG-2 oleylammonium chloride and salts of these, where the chloride is replaced by other halide (e.g., bromide), acetate, citrate, lactate, glycolate, phosphate nitrate, sulphate, or alkylsulphate.

In a preferred class of cationic surfactant of the above general formula, $R^1$ is a $C_{16}$ to $C_{22}$ saturated or unsaturated, preferably saturated, alkyl chain and $R^2$, $R^3$ and $R^4$ are each independently selected from $CH_3$ and $CH_2CH_2OH$, preferably $CH_3$.

Specific examples of such preferred quaternary ammonium cationic surfactants for use in forming the conditioning gel phase are cetyltrimethylammonium chloride (CTAC), behenyltrimethylammonium chloride (BTAC) and mixtures thereof.

Mixtures of any of the above-described cationic surfactants may also be suitable.

The level of cationic surfactant suitably ranges from 0.1 to 10 wt %, preferably from 0.2 to 5 wt % and more preferably from 0.25 to 4 wt % (by total weight of cationic surfactant based on the total weight of the composition).

By "high melting point" in the context of this invention is generally meant a melting point of 25° C. or higher. Generally the melting point ranges from 25° C. up to 90° C., preferably from 40° C. up to 70° C. and more preferably from 50° C. up to about 65° C.

The high melting point fatty alcohol can be used as a single compound or as a blend or mixture of at least two high melting point fatty alcohols. When a blend or mixture of fatty alcohols is used, the melting point means the melting point of the blend or mixture.

Suitable fatty alcohols of this type have the general formula R—OH, where R is an aliphatic carbon chain. Preferably R is a saturated aliphatic carbon chain comprising from 8 to 30 carbon atoms, more preferably from 14 to 30 carbon atoms and most preferably from 16 to 22 carbon atoms.

R can contain, in addition to carbon and hydrogen atoms, ether linkages, and other groups such as amino groups.

Most preferably, the fatty alcohol has the general formula $CH_3(CH_2)_n$ OH, where n is an integer from 7 to 29, preferably from 15 to 21.

Specific examples of suitable fatty alcohols are cetyl alcohol, stearyl alcohol, behenyl alcohol, and mixtures thereof. Cetyl alcohol, stearyl alcohol and mixtures thereof are particularly preferred.

Mixtures of any of the above-described fatty alcohols may also be suitable.

The level of fatty alcohol suitably ranges from 0.01 to 10 wt %, preferably from 0.1 to 8 wt %, more preferably from 0.2 to 7 wt % and most preferably from 0.3 to 6 wt % (by weight based on the total weight of the composition).

The weight ratio of cationic surfactant to fatty alcohol is suitably from 1:1 to 1:10, preferably from 1:1.5 to 1:8, optimally from 1:2 to 1:5.

A hair shaping composition according to the invention may also incorporate other optional ingredients to enhance performance and/or consumer acceptability. Suitable optional ingredients include: preservatives, colouring agents, chelating agents, antioxidants, fragrances, antimicrobials, antidandruff agents, cationic conditioning polymers, styling ingredients, sunscreens, proteins and hydrolysed proteins.

Preferably, the hair shaping composition is a single dose composition. The term "single dose" in the context of this invention means that the composition is to be topically applied to the hair in one go.

The hair shaping composition of the invention is suitable for topical application to hair for improved hair volume-down. The term "volume-down" in the context of this invention generally means reduced visible bulkiness of the hair. For many consumers, improved hair volume-down provides a number of associated benefits, such as improved straightness, smoothness, manageability and style retention.

The hair shaping composition of the invention is preferably topically applied to the hair at a temperature from 15 to 40° C., and more preferably at a temperature from 20 to 30° C.

Preferably, the composition is applied to dry hair. The term "dry hair" in the context of this invention generally means hair from which free water (i.e. water disposed as a film or droplets on the cuticle surface) has been substantially removed. Hair may be dried by exposure to air, by use of a heated hair drying appliance, by rubbing with a water-absorbent article, or by a combination of any of these methods. Preferably, the dry hair will not have been washed or actively wetted, (such as by shampooing, conditioning, rinsing or otherwise treating with an aqueous composition) in the preceding 2 hours and more preferably in the preceding 3 hours prior to topical application of the composition, and will have been permitted to acclimatise to atmospheric conditions. In such circumstances there is substantially no free water present which interferes with the adsorption of the composition on application. A suitable indicator of dry hair in the context of this invention would be a hair fibre whose calculated water content does not exceed 25 wt % by weight based on the total weight of the hair fibre.

After topical application to the hair, it is preferred that the hair shaping composition is allowed to remain in contact with the hair without rinsing. More preferably, the hair shaping composition is allowed to remain in contact with the hair without rinsing until the hair thus treated is dry.

The hair thus treated may be dried naturally by exposure to air, by use of a heated hair drying appliance, by rubbing with a water-absorbent article, or by a combination of any of these methods.

The hair shaping composition may thus remain in contact with the hair after topical application for a period of at least about 3 minutes up to 3 hours or more if the hair is allowed to dry naturally.

In step (ii) of the method of the invention, the treated hair is shaped.

Shaping of the hair in the method of the invention can be accomplished by such means as the finger tips, a plastic hair pick or the tail of a comb, the shaping being performed on portions of the hair comprising strands of hair in various numbers. Using such means the hair may be pulled, combed, smoothed, pressed or flattened into a straightened configuration; or shaped gently into bends, waves or curls.

Preferably in step (ii) of the method of the invention, the hair is mechanically straightened. For example, the hair may be pulled, combed, smoothed, pressed or flattened into a straightened configuration.

A hot tool, such as an electrically heated flat hair iron or hand-held hair dryer, may be used in the mechanical shaping step. Such tools apply high levels of heat directly to the hair. Most operate in the 45° C. to 250° C. range, and are usually employed at temperature settings ranging from 50° C. to about 220° C., depending on the particular tool.

Particularly good results have been obtained when the hair is mechanically straightened in step (ii) of the method of the invention with a hot tool such as an electrically heated flat hair iron. In such a case, it is preferred that the operating temperature of the hot tool ranges from 120 to 220° C., more preferably from 150 to 220° C., and most preferably from 170 to 220° C.

In a typical method for shaping hair according to the invention, the hair shaping composition is topically applied to dry hair and the hair thus treated is combed straight at a temperature from 15 to 40° C., preferably at a temperature from 20 to 30° C. The treated, combed hair is dried (or allowed to dry) without rinsing the composition from the hair, and the dry hair is then mechanically straightened with a hot tool at an operating temperature from 120 to 220° C., preferably from 150 to 220° C., and more preferably from 170 to 220° C.

The hair shaping composition may then be rinsed from the hair at the next wash.

Surprisingly, the inventors have found that the improved "volume-down" provided by the hair shaping composition in accordance with the invention is capable of persisting after washing.

Accordingly the invention also provides a method for shaping and re-shaping hair comprising the following steps:
(i) treating the hair by topical application of a hair shaping composition as defined above;
(ii) mechanically shaping the treated hair;
(iii) rinsing the shaped hair, and
(iv) mechanically re-shaping the rinsed hair.

In a typical method for shaping and re-shaping hair according to the invention, the hair shaping composition is topically applied to dry hair and the hair thus treated is combed straight at a temperature from 15 to 40° C., preferably at a temperature from 20 to 30° C. The treated, combed hair is dried (or allowed to dry) without rinsing the composition from the hair, and the dry hair is then mechanically straightened with a hot tool at an operating temperature from 120 to 220° C., preferably from 150 to 220° C., and more preferably from 170 to 220° C. The hair shaping composition is then rinsed from the hair at the next wash: typically after a period of about 24 to 72 hours following the initial application of the composition in step (i). The rinsed hair is then mechanically re-shaped.

The rinsing step may be conducted with water alone or with shampoo.

The use of hot tools is not essential in the re-shaping step. This is especially advantageous for consumers who wish to reduce or avoid the exposure of their hair to high temperatures, for example if their hair is fragile or overprocessed from previous chemical treatments such as bleaching and perming.

Accordingly the hair is preferably re-shaped by combing it into a straightened configuration at a temperature from 15 to 40° C., more preferably at a temperature from 20 to 30° C.

Method steps (i) to (iv) as described above may also be repeated over one or more (e.g. two or three) cycles.

The invention is further illustrated with reference to the following, non-limiting Example.

EXAMPLE

All ingredients are expressed by weight percent of the total formulation, and as level of active ingredient.

Dark brown European wavy#6 switches were soaked for 20 minutes in solutions of 3% glyceraldehyde (comparative), 3% urea (comparative) and a combination of the two (according to the invention). Control switches were soaked in water.

All switches were combed straight and were dried in drying cabinets.

When dry the switches were ironed with 5-7 passes using straighteners at 200° C. After 2 days they were washed with shampoo and combed straight and dried in drying cabinets. When dry the switches were combed and pictures taken. This was repeated for another wash. No heat styling was done after the initial ironing stage prior to the first wash.

The volumes of the switches were measured using an image analysis kit. The volume of the switches shows the volume-down (straightness) benefits of the treatment (here volume refers to the projection of the switch image on to the screen and is given in $mm^2$). The percentage benefit (i.e. decrease in volume) with respect to control (water) is also given.

The results are shown in Table 1.

TABLE 1

Volumes of treated hair switches in $mm^2$ after a single heat treatment and subsequent two washes after 2 days each

| | after 1st wash | | after 2nd wash | |
|---|---|---|---|---|
| Treatment | volume | % benefit | volume | % benefit |
| water (control) | 15492 | 0.0 | 16176 | 0.0 |
| 3% urea | 16646 | −7.4 | 16979 | −5.0 |
| 3% glyceraldehyde | 13105 | 15.4 | 12566 | 22.3 |
| 3% urea + 3% glyceraldehyde | 11904 | 23.2 | 10540 | 34.8 |

The results show that the treatment with urea and glyceraldehyde according to the invention gives excellent hair volume-down (straightness) benefits compared to the control.

The results also show that the treatment with urea and glyceraldehyde according to the invention gives excellent hair volume-down (straightness) benefits compared to the comparative examples with either ingredient on its own. It is clear that the combination of urea and glyceraldehyde according to the invention has a synergistic effect.

BRIEF DESCRIPTION OF THE DRAWING

The FIGURE is a picture showing the effect of the treatment with urea and glyceraldehyde according to the invention after 1 treatment and 2 washes. The volume-down (straightness) benefit is clearly evident from a visual comparison between the left hand picture (control) and the right hand picture (according to the invention).

The invention claimed is:

1. A hair straightening composition suitable for topical application to hair, the hair straightening composition comprising:
   1 to 5 wt % of glyceraldehyde; and
   1 to 5 wt % of a urea compound of the general formula:

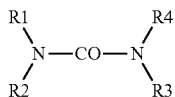

wherein:
   R1, R2, R3, and R4 are each hydrogen;
   the glyceraldehyde and urea are dissolved in an aqueous carrier; and
   the wt % amounts are based on the total weight of the hair straightening composition.

2. The hair straightening composition of claim 1, wherein the hair straightening composition comprises a weight ratio of glyceraldehyde to urea of 5:1 to 1:2.

3. The hair straightening composition of claim 2, wherein the weight ratio is from 3:1 to 2:3.

4. The hair straightening composition of claim 2, wherein the weight ratio is 1:1.

5. The hair straightening composition of claim 1, wherein the hair straightening composition is substantially free of reducing agents selected from the group consisting of ammonium thioglycolate, glyceryl monothioglycolate, thioglycolic acid, dithioglycolic acid, mercaptoethyl amine, mercaptopropionic acid, dithioglycolate, and alkali metal or ammonium sulfites or bisulfites.

6. The hair straightening composition of claim 1, wherein the hair straightening composition comprises at least 60 wt % water based on the total weight of the hair straightening composition.

7. The hair straightening composition of claim 1, wherein the hair straightening composition further comprises a conditioning gel phase.

8. A method for straightening hair comprising:
   topically applying a hair straightening composition according to claim 1 to treat the hair, and
   mechanically straightening the treated hair.

9. The method of claim 8, wherein the hair straightening composition remains in contact with the treated hair until the treated hair is dry.

10. The method of claim 9, wherein the mechanical straightening comprises mechanically straightening the treated hair with a hot tool at an operating temperature from 120 to 220° C.

11. The method of claim 8, wherein the method further comprises:
    rinsing the straightened hair, and
    mechanically re-straightening the rinsed hair.

12. The method of claim 11, wherein rinsing the straightened hair occurs after a period of 24 to 72 hours following topically applying the hair straightening composition.

* * * * *